(12) United States Patent
Auerbach et al.

(10) Patent No.: US 6,302,842 B1
(45) Date of Patent: Oct. 16, 2001

(54) EPISIOTOMY RETRACTOR

(75) Inventors: Robert D. Auerbach; Richard D. Moscarelli, both of Madison, CT (US)

(73) Assignee: Innovative Surgical Design LLC, Madison, CT (US)

( * ) Notice: Subject to any disclaimer, the term of this patent is extended or adjusted under 35 U.S.C. 154(b) by 0 days.

(21) Appl. No.: 09/758,947

(22) Filed: Jan. 11, 2001

(51) Int. Cl.[7] .................................... A61B 17/02
(52) U.S. Cl. ..................... 600/220; 600/219; 600/235
(58) Field of Search .................. 600/219, 220, 600/222, 214, 226, 235, 210

(56) References Cited

U.S. PATENT DOCUMENTS

| | | | |
|---|---|---|---|
| 485,609 | * | 11/1892 | Casebeer ........................ 600/219 |
| 583,932 | * | 6/1897 | Pederson ........................ 600/219 |
| 831,592 | | 9/1906 | Ballard . |
| 1,894,725 | * | 1/1933 | Bacon ........................... 600/220 |
| 3,038,467 | * | 6/1962 | Sovatkin ........................ 600/219 |
| 3,176,682 | | 4/1965 | Wexler . |
| 3,716,047 | | 2/1973 | Moore et al. . |
| 3,841,317 | | 10/1974 | Awais . |
| 3,893,454 | * | 7/1975 | Hagelin ......................... 600/219 |
| 4,690,132 | | 9/1987 | Bayer et al. . |
| 4,754,746 | | 7/1988 | Cox . |
| 5,007,409 | | 4/1991 | Pope . |
| 5,167,222 | | 12/1992 | Schinkel et al. . |
| 5,785,648 | | 7/1998 | Min . |
| 5,885,210 | * | 3/1999 | Cox ............................. 600/219 |
| 5,899,854 | | 5/1999 | Slishman . |
| 5,931,777 | | 8/1999 | Sava . |
| 6,024,697 | | 2/2000 | Pisarik . |
| 6,042,540 | * | 3/2000 | Johnston et al. ................ 600/219 |

* cited by examiner

Primary Examiner—Paul J. Hirsch
(74) Attorney, Agent, or Firm—Amster, Rothstein & Ebenstein

(57) ABSTRACT

In an episiotomy retractor, distal portions of the blades are shaped to diverge away from one another for enhanced retraction and gripping of respective adjacent vaginal walls, proximal portions of the blades are shaped to diverge away from one another to retract the labia as the blades retract respective adjacent vaginal walls, and the proximal inferior longitudinal edges of the blades cooperatively define, when the retractor is in use, an open work area for a surgeon about the perineum and the posterior vaginal wall of a patient.

25 Claims, 9 Drawing Sheets

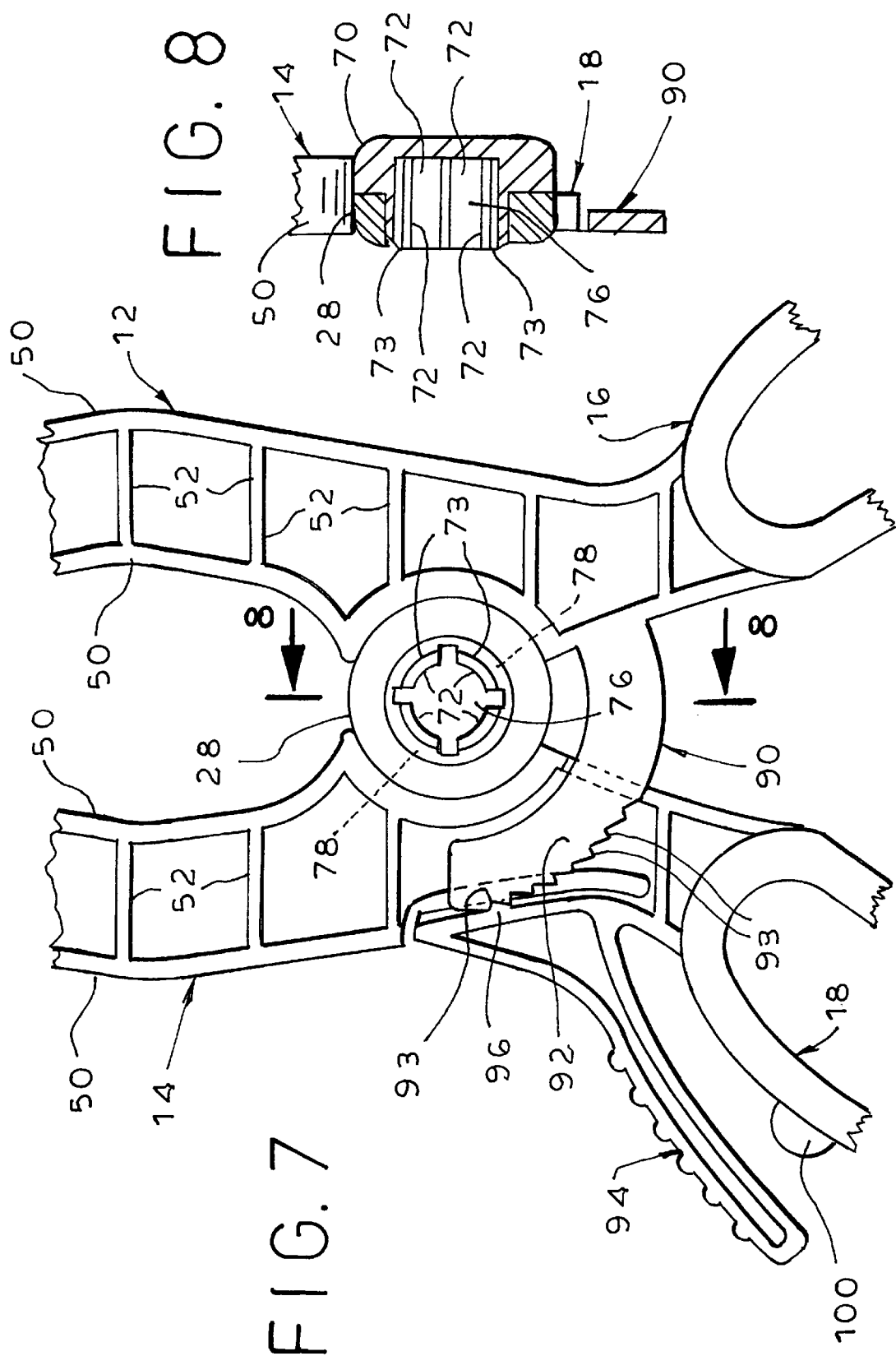

EPISIOTOMY RETRACTOR

BACKGROUND OF THE INVENTION

The present invention relates to an episiotomy retractor and, more particularly, to such a retractor which provides a superior open work area for a surgeon about the perineum and the posterior vaginal wall of the patient.

It is well known to provide an episiotomy retractor for retracting friable postpartum vaginal tissue in order to facilitate repair of the episiotomy or vaginal laceration. The primary function of the retractor is provide an open work area for the surgeon about the perineum and posterior vaginal wall of the patent so that the surgeon can conveniently and safely approximate and suture the tissue planes to complete repair.

The known episiotomy retractors have not proven to be entirely satisfactory in use. They are frequently made of metal, which can be perceived by a patient as cold and hard. The metal retractors are heavy and hence prone to shifting during use. The blades are typically either flat or convexly curved in section, with the result that during use the retractor may slip while the surgeon is attempting to perform sutures. This can result in needle sticking of the distal forefinger or thumb of the non-dominant hand of the surgeon when the same is used to guide needle placement or exposed tissue planes, thereby possibly exposing the surgeon to infectious disease. Currently no retractor exists which enhances exposure of vaginal and perineum tissue while at the same time reducing the chance of needle stick injury at the time of episiotomy and/or vaginal laceration repair.

Most importantly, the conventional retractors fail to provide sufficient open work area for the surgeon about the perineum and the posterior vaginal wall of the patient. During the delivery process the labia of the patient become engorged with blood and thus tends to interfere with visualization of the desired work area by the surgeon. Accordingly, the need remains for a retractor which not only retracts the vaginal tissue, but is also operative to retract the swollen labia to facilitate visualization and provide relatively easy access to the work area.

The problems discussed above are aggravated where the patient has not received epidural anesthesia since the patient is more likely to experience the pain involved in retraction of the vaginal walls and piercing of the tissue during suturing. The pain experienced by the unanesthetized patient may result in voluntary and/or involuntary movements by the patient, thereby interfering with the procedure being performed. As a result, the likelihood of retractor slippage and/or needle stick of the surgeon is increased.

Accordingly, an object of the present invention is to provide an episiotomy retractor which affords an open work area of desirable size for a surgeon about the perineum and the posterior vaginal wall of the patient.

Another object is to provide such a retractor which is lightweight and configured and dimensioned to minimize slippage during use.

A further object is to provide such a retractor which will retract the engorged labia of the postpartum patient as well as the vaginal walls.

It is also an object of the present invention to provide such a retractor which minimizes discomfort to the patient and the possibility of needle stick to the surgeon.

It is another object to provide such a retractor which is simple and inexpensive to manufacture, use and maintain.

SUMMARY OF THE INVENTION

It has now been found that the above and related objects of the present invention are obtained in an episiotomy retractor according to the present invention comprising, in combination, first and second scissors arms bearing first and second blades, respectively. The first scissors arm includes a manual gripping end and a support shaft end, and the second scissors arm includes a manual gripping end and a support shaft end, the first and second arms being coupled together intermediate their respective ends to permit movement of the first and second arms relative to one another. The first blade is positioned proximate the first arm support shaft end and includes a mounting end mounted to the first arm support shaft end and a free insertion end, and the second blade is positioned proximate the second arm support shaft end and includes a mounting end mounted to the second arm support shaft end and a free insertion end, the first and second blades being generally parallel whereby the first and second blades are in generally opposed relation and whereby, as the gripping ends move relative to one another, the blades move relative to one another.

Each blade defines superior and inferior longitudinal edges, and, as the support shaft ends move apart, the superior longitudinal edges of the blades become transversely spaced apart from each other to a greater degree than the inferior longitudinal edges of the blades. Distal portions of the blades proximate the insertion ends are shaped to diverge away from one another for enhanced retraction and gripping of respective adjacent vaginal walls to stabilize the orientation of the retractor relative to the vagina of a patient. Proximal portions of the blades proximate the mounting ends are shaped to diverge away from one another to retract the labia as the blades retract respective adjacent vaginal walls. Facing opposed longitudinal edges of the arms proximate the support shaft ends and the proximal inferior longitudinal edges of the blades cooperatively define, when the retractor is in use, an open work area for a surgeon about the perineum and the posterior vaginal wall of a patient.

The gripping ends of the first and second arms are generally aligned. As the gripping ends move together, the support ends move apart, and vice versa. As the gripping ends move apart, the superior longitudinal edges of the blades become transversely spaced apart from each other to a greater degree than the inferior longitudinal edges of the blades.

Preferably the arms are pivotable in a plane, the blades extend at a generally transverse angle from the plane of the arms. The blades are substantially identical and affixed to the support shaft ends in opposed, mirror image relationship, the proximal inferior longitudinal edges of the blades being concavely curved (e.g., with a radius of curvature of about 1.4 inch) to maximize the open work area. Optimally the blades insertion ends curve divergently away from each other at an included angle of about 40°, and the blade mounting ends curve divergently away from each other at an included angle of about 30°.

In a preferred embodiment each arm defines peripheral flanges longitudinally extending intermediate the gripping end and the support shaft end and a series of longitudinally spaced ribs extending transversely between the peripheral flanges to rigidify the arm, the arm peripheral flanges and ribs being downwardly disposed; and each blade defines a pair of longitudinally extending peripheral flanges and a series of transversely spaced apart longitudinally extending ribs to rigidify the blade, the blade peripheral flanges and ribs being inwardly disposed.

In another preferred embodiment the retractor is formed of exclusively lightweight plastic. Each arm and its respective blade are of unitary, one-piece, integral construction formed in a single molding operation. The arms preferably include clamp members interacting to releasably maintain the arms in a manually adjusted, fixed orientation. Each blade preferably has an outwardly-facing surface textured for enhanced gripping.

BRIEF DESCRIPTION OF THE DRAWING

The above and related objects, features and advantages of the present invention will be more fully understood by reference to the following detailed description of the presently preferred, albeit illustrative, embodiments of the present invention, when taken in conjunction with the accompanying drawing wherein:

FIG. 7 is a fragmentary rear elevational view thereof showing the interconnection of the scissor arms;

FIG. 8 is a fragmentary sectional view taken along the line 8—8 of FIG. 7; and

DETAILED DESCRIPTION OF THE PREFERRED EMBODIMENTS

Figure 1:
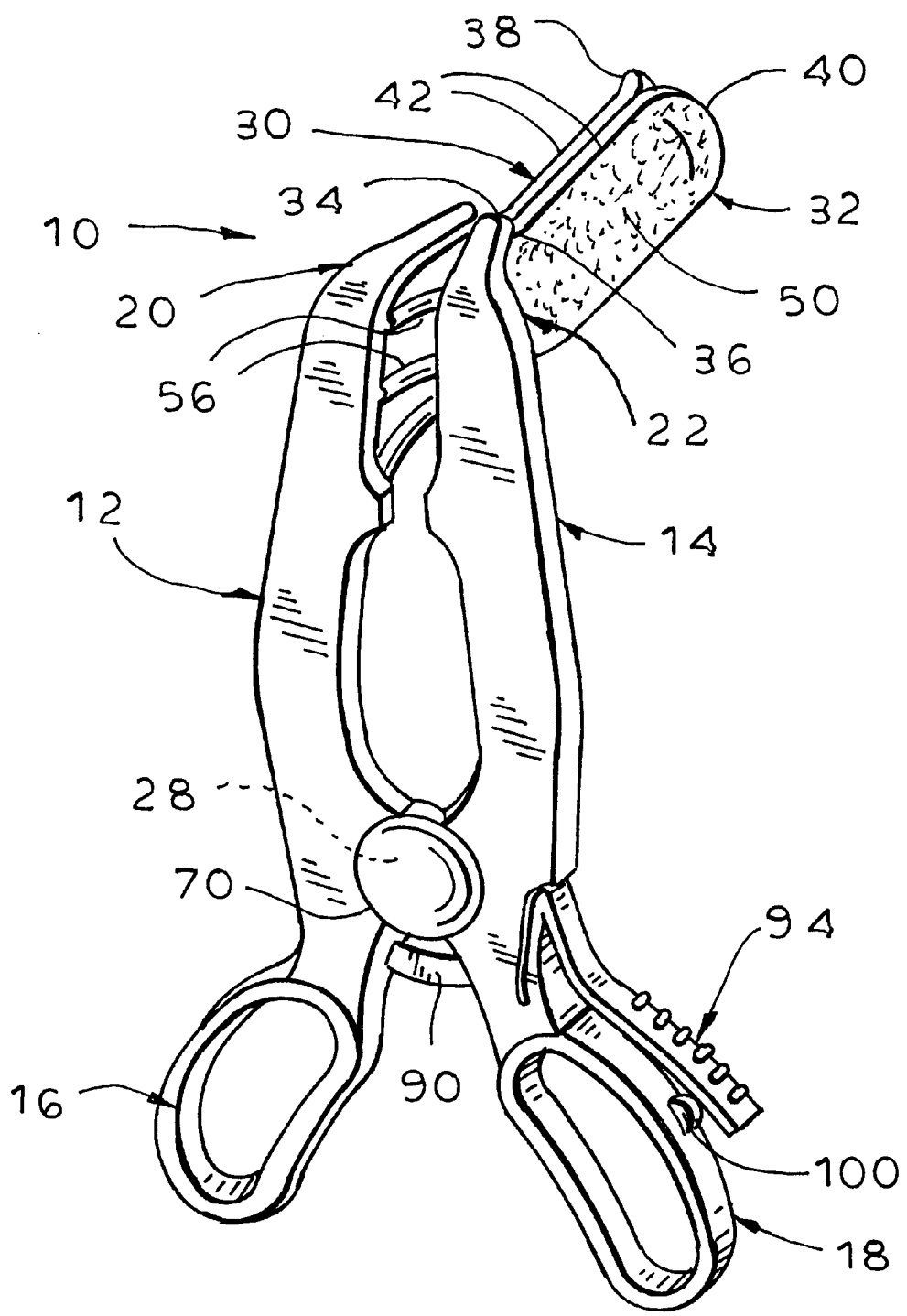
FIG. 1 is an isometric view of an episiotomy retractor according to the present invention.
Figure 2:
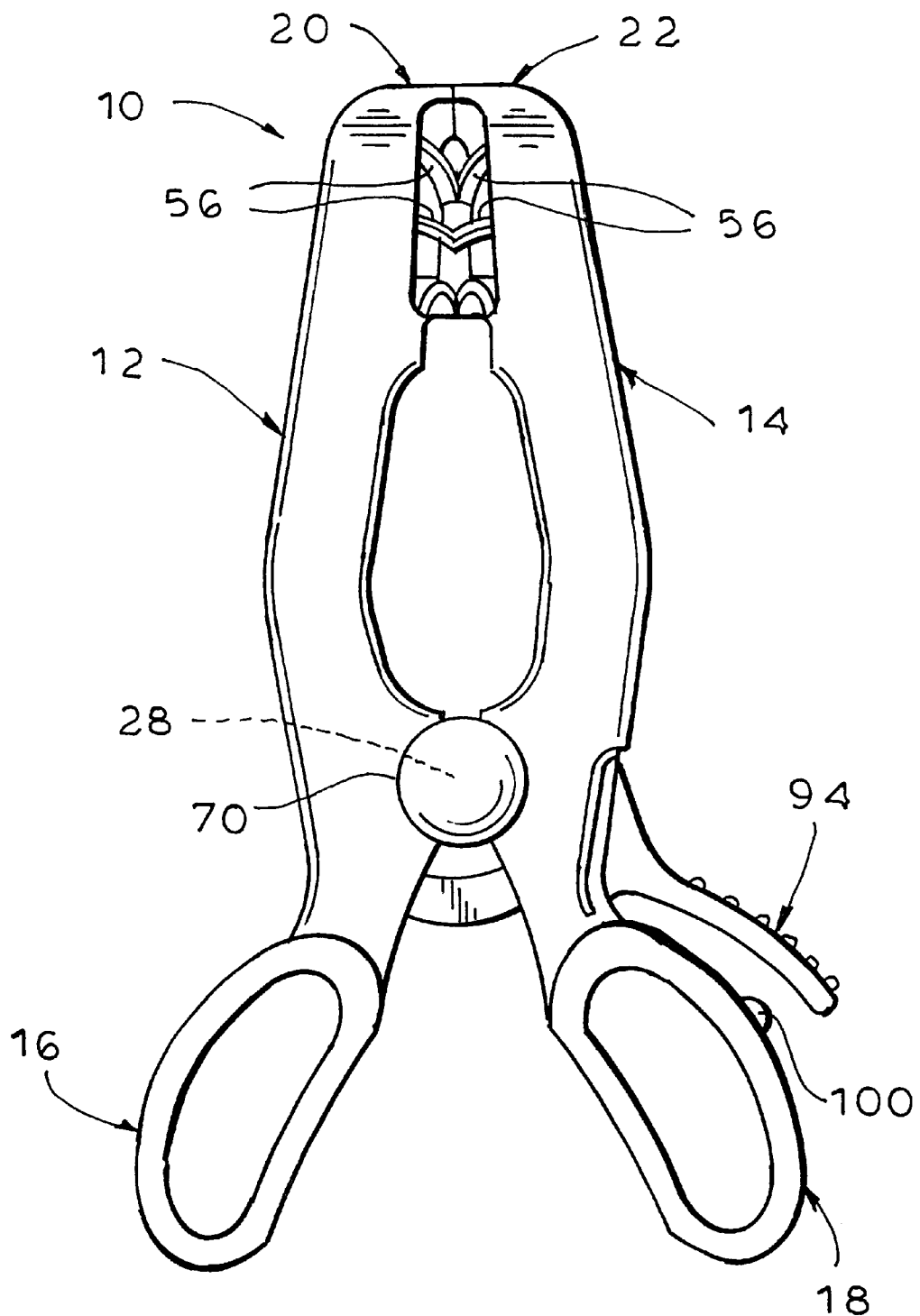
FIG. 2 is a front elevational view thereof.

Referring now to the drawing, and in particular to FIGS. 1–4 thereof, therein illustrated in a closed orientation is an episiotomy retractor according to the present invention, generally designated by the reference numeral 10. The retractor 10 comprises, in combination, a first scissor arm, general designated 12, and a second scissor arm, generally designated 14. Each scissor arm 12, 14 includes a first or manual gripping end, generally designated 16, 18, and a second or support shaft end, generally designated 20, 22, respectively. The gripping ends 16, 18 are in a generally opposed relationship, and the mounting ends 20, 22 are in a generally opposed relationship. The gripping ends 16, 18 and mounting ends 20, 22 are generally aligned in the same plane. The manual gripping ends 16, 18 are loop-like in configuration, and each defines an aperture therethrough for receipt of a user's finger(s), much like an ordinary pair of scissors.

The first and second scissor arms 12, 14 are coupled together at 28, intermediate their respective ends 16, 20 and 18, 22 to permit movement of the first and second arms 12, 14 relative to one another. It is to be appreciated, however, that, unlike a conventional pair of scissors where movement of the manual gripping ends together brings the opposed cutting ends together, in the retractor 10 movement of the manual gripping ends 16, 18 together separates the opposed support shaft ends 20, 22. This is due to the difference between the X-shaped configuration of conventional scissors relative to the H-shaped configuration of the present invention. The coupling together of arms 12, 14 at 28 will be discussed further hereinbelow in connection with FIGS. 7–9.

A first blade 30 is positioned proximate to the first arm support shaft end 20, and a second blade 32 is positioned proximate to the second arm support shaft end 22. The first and second blades 30, 32 extend generally parallel to one another at a generally transverse angle to the common plane of the scissor arms 12, 14. The blades 30, 32 are substantially identical and positioned proximate the support shaft ends 20, 22, respectively, in a generally opposed mirror image relationship. The first and second blades 30, 32 are mounted on the support shaft ends 20, 22, respectively, such that, as the gripping ends 16, 18 move relative to one another, the support shaft ends 20, 22 and the blades 30, 32 mounted thereon move relative to one another as well.

Figure 3:
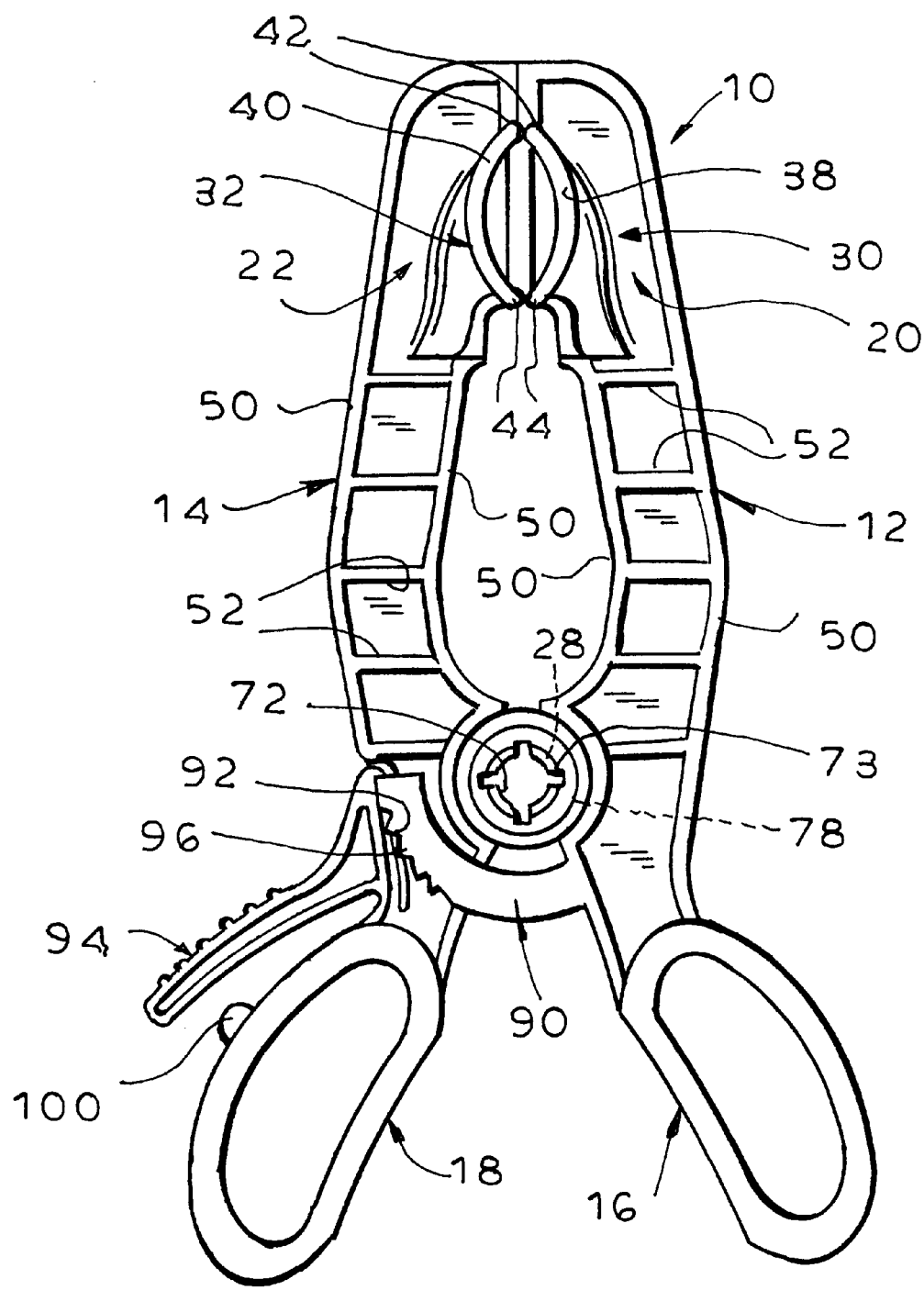
FIG. 3 is a rear elevational view thereof.
Figure 4:
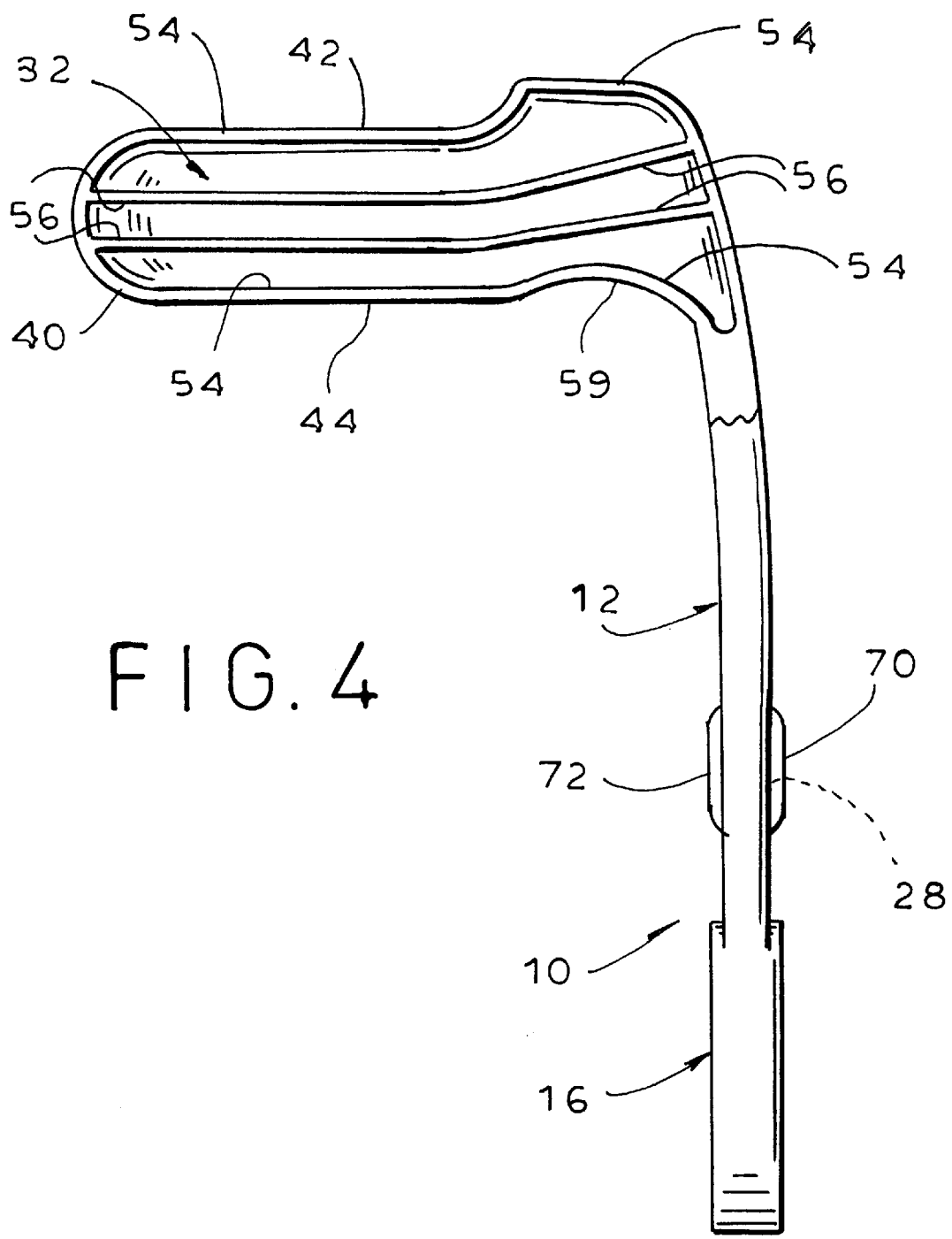
FIG. 4 is a side elevational view thereof, with a portion thereof cut away to reveal details of construction.

Each of the first and second blades 30, 32 includes a mounting end 34, 36 mounted to a respective support shaft end 20, 22 and a free insertion end 38, 40, respectively. Each blade 30, 32 defines superior (or upper) longitudinal edges 42 (as seen in FIGS. 1 and 3–4) and inferior (or lower) longitudinal edges 44 (as best seen in FIGS. 3–4). As the support shaft ends 20, 22 move apart, the superior longitudinal edges 42 of the blades becomes transversely spaced apart from each other to a greater degree than the inferior longitudinal edges 44.

In its basic outline as described hereinabove the episiotomy retractor 10 of the present invention is conventional in design. Accordingly, it is not deemed necessary to specify further details thereof herein.

The retractor 10 according to the present invention is preferably made of a lightweight surgical grade plastic to facilitate handling by the surgeon, to provide a "warmer" feel to the patient, and to reduce the likelihood of retractor slippage during use. A preferred plastic is medical grade polycarbonate available under the tradename GE Lexan HPS1 from GE. Preferably each arm 12, 14 and its respective blade 30, 32 is of unitary, one-piece, integral construction formed in a single molding operation. This, of course, facilitates the manufacturing process and greatly reduces the cost thereof.

Figure 5:
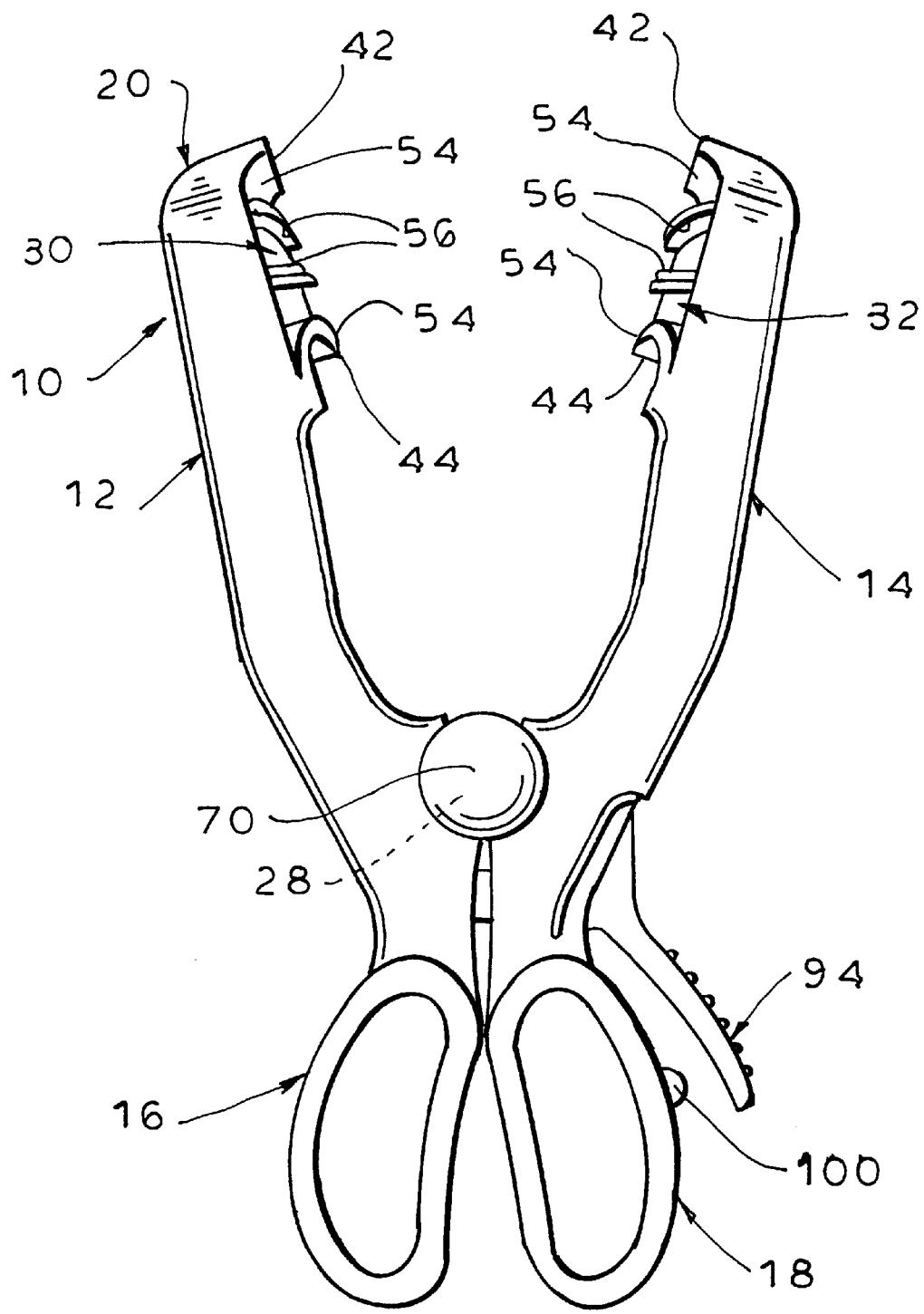
FIG. 5 is a front elevational view similar to FIG. 2, but showing the retractor in an open orientation.
Figure 6A:
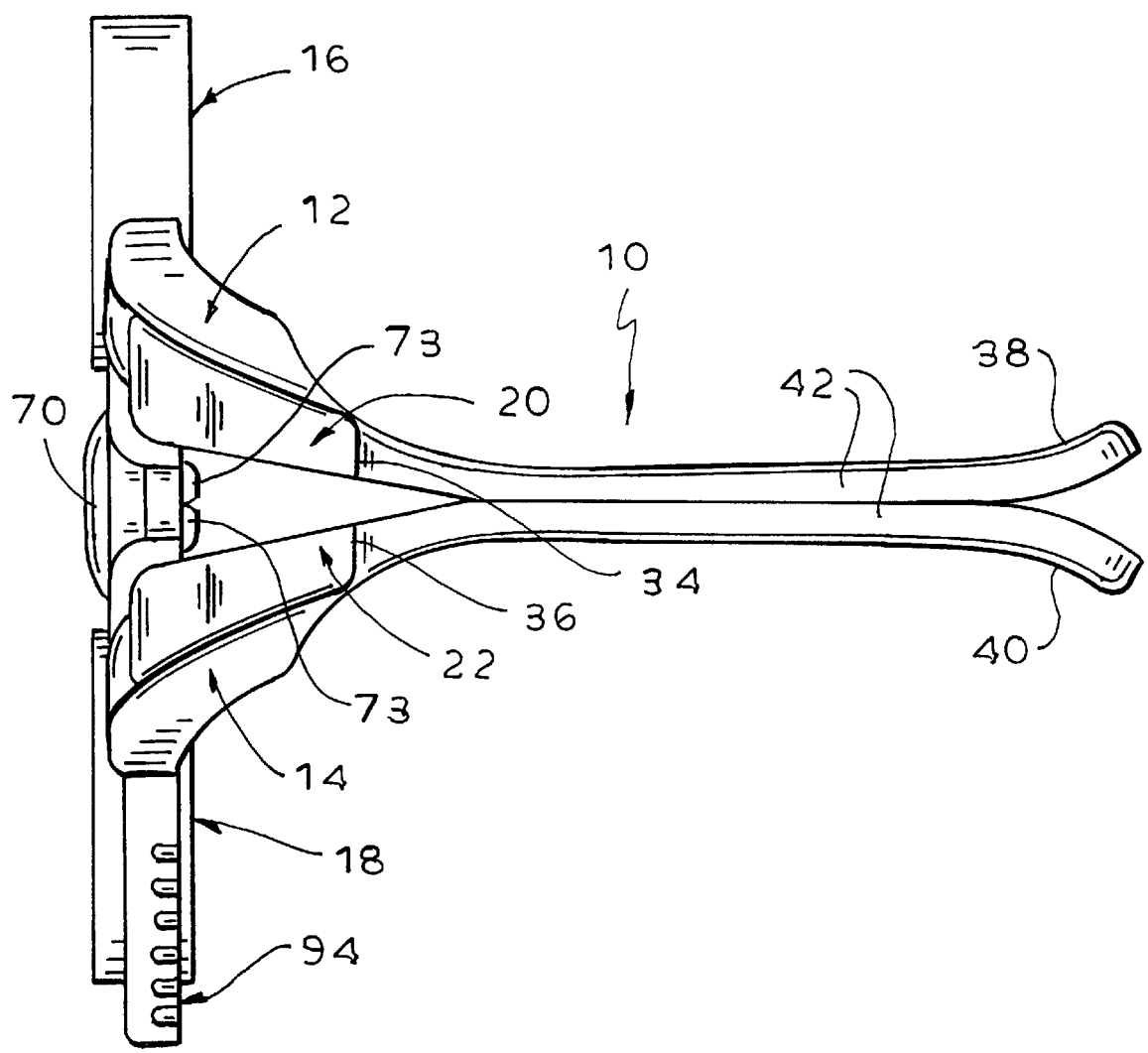
FIG. 6A is a top plan view thereof, in a closed orientation.
Figure 6B:
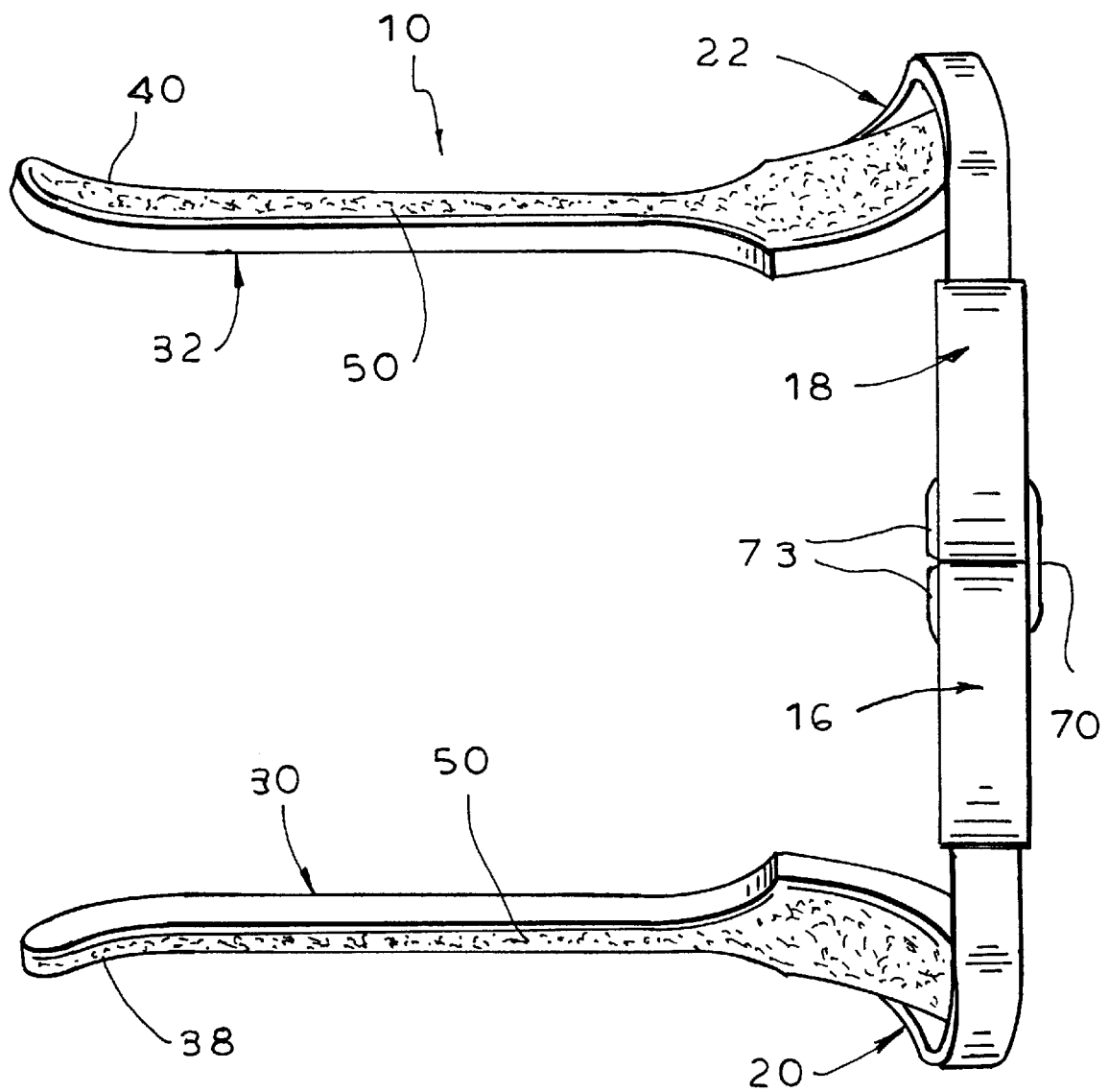
FIG. 6B is a bottom plan view thereof, in an open orientation.

In order to provide the structural integrity and stiffness required in the retractor 10 despite its construction of lightweight plastic, each arm and each blade is specially constructed. Thus, referring now to FIGS. 3–5 in particular, each arm 12, 14 defines peripheral flanges 50 extending intermediate the gripping end 16, 18 and the support shaft end 20, 22, respectively, as well as a series of longitudinally spaced ribs 52 extending transversely between the peripheral flanges 50 to rigidify the arm 12, 14. The arm peripheral flanges 50 and ribs 52 are rearwards disposed, preferably to about the same extent. Further, each blade 30, 32 defines a pair of longitudinally extending peripheral flanges 54 and a series of transversely spaced apart longitudinally extending ribs 56 to rigidify the blade. The blade peripheral flanges 54 and ribs 56 are inwardly disposed, preferably to about the same extent. Typically the longitudinally extending peripheral flanges 54 of the blades 30, 32 define the superior and inferior longitudinal edges 42, 44 thereof, as best seen in FIG. 5. The longitudinally extending peripheral flanges 54 of each blade 30, 32 extend towards the other and meet in a blunt curve at the downwardly converging ends 38, 40 thereof.

In order to further contribute to stabilization of the retractor 10 in a selected orientation during use, the distal portions 38, 40 of the blades 20, 22, respectively, are shaped to diverge away from one another for enhanced retraction and gripping of respective adjacent vaginal walls of the patient during use, thereby stabilizing the orientation of the retractor 10 relative to the patient's vagina. Preferably the insertion ends 38, 40 curve divergently away from each other at an included angle of about 40°±5°. As the diverging insertion ends 38, 40 define a relatively flat (blunt), smooth curve, they will ordinarily not be painful during use and hence are suitable for use even on an unanesthetized patient.

To further enhance fixation of the retractor 10 in a selected orientation during use, the outside surface of each blade 30, 32 defines raised texturing, thereby to enhance secure grasping of the vaginal walls of the patient by the blades.

Just as the distal portions of the blades 30, 32 proximate the insertion ends 38, 40, respectively, are shaped to diverge away from one another for enhanced retraction and gripping of respective adjacent vaginal walls, the proximal portions of the blades 30, 32 proximate the mounting ends 34, 36, respectively, are shaped to diverge away from one another to retract the labia as the blades 30, 32 retract respective adjacent vaginal walls. Preferably the mounting ends 34, 36 curve divergently away from each other at an included angle of about 30°±5° where they terminate in the support shaft ends 20, 22 of the scissor arms 12, 14, respectively. As the blade mounting ends 34, 36 retract the blood-engorged postpartum labia, the field of visualization and the open work area for the surgeon are greatly improved by the retractor 10 of the present invention.

Interestingly, while both the blade distal portions proximate the insertion ends 38, 40 and the blade proximal portions proximate the mounting ends 34, 36 are both shaped to diverge away from one another, their functions are quite unrelated. The blade distal portions enhance retraction and gripping of adjacent vaginal walls to stabilize the orientation and gripping of the retractor, while the blade proximal portions retracting the labia to enhance visualization and increase the open work area for the surgeon. Nonetheless, these opposite blade portions cooperate in the present inventions to provide the surgeon with a superior retractor 10 affording more reliable orientation, better visualization, and an increased open work area.

In the preferred embodiment of retractor 10 illustrated, and as best seen in FIG. 4, the facing opposed longitudinal edges of the arms 12, 14 proximate the support ends 20, 22 in combination with the proximate inferior longitudinal edges 44 of the blades 30, 32 cooperatively define, when the retractor 10 is in use, an open work area for a surgeon about the perineum and posterior vaginal wall of the patient. The proximal inferior longitudinal edges 44 of the blades 30, 32 are preferably concavely curved at 59 to maximize the open work area. Preferably the radius of curvature defined by each such edge 44 (and thus by each inferior longitudinally extending peripheral flange 54) is about 1.0–2.0 inches, optimally about 1.4 inches.

Figure 9:
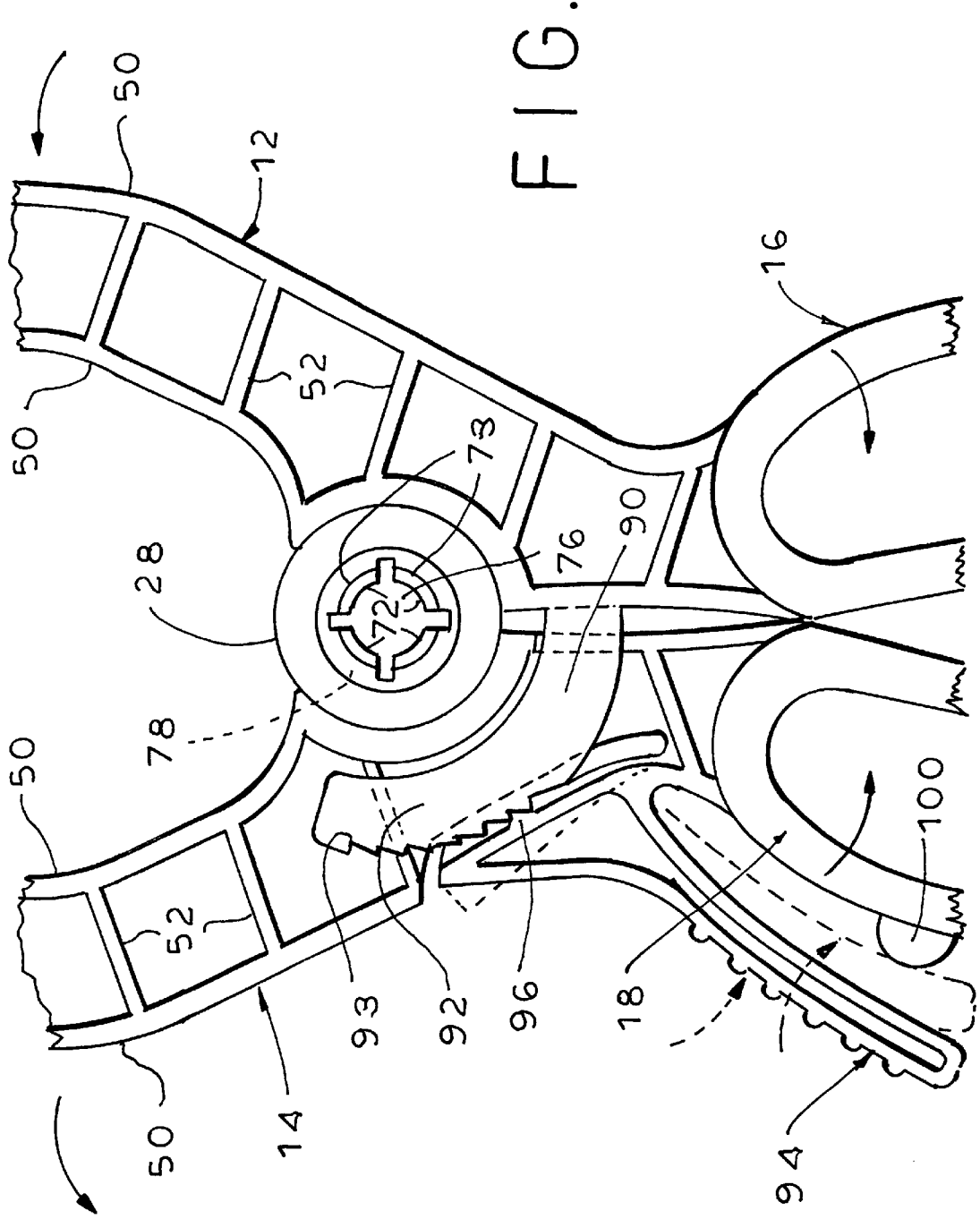
FIG. 9 is a fragmentary rear elevational view similar to FIG. 7, but showing the retractor in an open orientation with a depressed lever.

Returning now to the scissor arms 12, 14 and the pivotal connection therebetween at 28, and referring now to FIGS. 7–9 in particular, one arm 12, 14 (as illustrated, arm 14) defines a front circular cover 70 which is relatively smooth and continuous on its front surface and a plurality (here, four) of circumferentially spaced, rearwardly extending, and outwardly resilient biased lugs 72. Each lug 72 defines at its rear end an outwardly extending flange 73. The other arm 14, 12 (as illustrated, arm 12) defines an aperture 76 therethrough and a rear rim 78. To assemble the arms 12, 14 in pivotal relationship at 28, lugs 72 are squeezed together and inserted rearwardly through the aperture 76 until the front face of rim 78 and the rear face of front cover 70 abut. At this point the lugs 72 will extend through the component 78 and may be released so that the outwardly extending rear end flanges 73 will extend outwardly over the rim 78 to maintain the pivotal connection, while still allowing relative pivotal movement of arm 14 (including front cover 70, lugs 72 and flanges 73) and arm 12 (including rear rim 78). As will be appreciated by those skilled in the art, a variety of other pivotal connections between arms 12, 14 may be made instead without departing from the principles of the present invention. The connection mechanism illustrated has the advantages of simplicity, ease of assembly and reliability, all without the need for the introduction of additional elements into what is essentially a two-component retractor wherein each arm and its respective blade are of unitary, one-piece, integral construction formed in a single molding operation.

The arms 12, 14 preferably include clamp member portions interacting to releasably maintain the arms in a manually adjusted, fixed relative orientation. Thus, in the illustrated right-handed version of the retractor 10, the scissor arm 12 includes an arcuate clamp member, generally designated 90, extending partially around the pivot connection at 28 and defining along an outer surface thereof a serrated edge 92 with teeth 93. The scissor arm 14 includes an outwardly biased, resilient clamp member lever, generally designated 94, which defines a single detent 96 that, in the unflexed state of lever 94, bears against and engages one of the teeth 93 of the serrated edge 92 of the arcuate clamp member 90 of arm 12. The free end portion of lever 94 is resiliently biased outwardly of the manual gripping end 18 but may easily and conveniently be forced by the finger(s) of the surgeon's hand holding the retractor 10 towards the gripping end 18, as illustrated in phantom line in FIG. 9. This forcible pivoting of the lever 94 about a pivot point generally indicated at 98 results in a withdrawal of the detent 96 from the previously engaged tooth 93 of the serrated edge 92. At this point, the surgeon can freely adjust the relative position of the gripping ends 16, 18 (and thus the blades 30, 32) as desired, with subsequent release of the pressure exerted on lever 94 by the surgeon's fingers allowing the lever 94 and its detent 96 to return to its original position, but with the detent 96 engaging a different tooth 93 of serrated edge 92. If desired, the outer surface of gripping end 18 may be provided with a stop 100 to limit forcible inward movement of the lever 94 beyond that which is required to disengage the detent 96 and the tooth 93. The ability of the surgeon to actuate and deactuate the clamping mechanism 90, 94 as necessary for manual readjustment of the relative orientation of retractor arms 12, 14 greatly facilitates one-handed use of the retractor by the surgeon.

Preferably, as illustrated, the teeth 93 of serrated edge 92 and the detent 96 are constructed so that movement of the gripping ends 16, 18 towards one another (and hence movement of the support shaft ends 20, 22 and their respective blades 30, 32 away from one another) does not require actuation of lever 94, such actuation being required only in order to separate gripping ends 16, 18 (and hence movement of support shaft ends 20, 22 and their blades 30, 32 towards one another). Thus, movement of the retractor 10 from the relatively closed orientation of FIG. 7 to the relatively open orientation of FIG. 9 preferably does not require manual actuation of the lever 94 because the required outward pivoting of lever 94 results from the natural interaction between the detent 96 and the teeth 93 of serrated edge 92 as the gripping ends 16, 18 are forcibly moved toward one another. The illustration in phantom line of the position of lever 94 in a depressed orientation (as would be caused by force along the phantom line arrow of FIG. 9) is that required to enable movement of the retractor from the relatively open configuration of FIG. 9 into the relatively closed configuration of FIG. 7. While clearly other clamp mechanisms may be used instead of clamp mechanism 90, 94, the illustrated mechanism is preferred as it does not require the use of additional components manufactured in a separate operation.

It will, of course, be obvious that the clamping members described above may be reconfigured as necessary to provide a left-handed retractor.

To summarize, the present invention provides an episiotomy retractor which affords an open work area of desirable size for a surgeon about the perineum and the posterior vaginal wall of the patient. It is lightweight and configured and dimensioned to minimize slippage during use. Additionally, it retracts the engorged labia of the postpartum patient as well as the vaginal walls and minimizes both discomfort to the patient and the possibility of needle stick to the surgeon. The retractor is simple and inexpensive to manufacture, use and maintain.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. An episiotomy retractor comprising, in combination:
   (A) a first scissors arm, including a manual gripping end and a support shaft end;
   (B) a second scissors arm, including a manual gripping end and a support shaft end, said first and second arms being coupled together intermediate their respective ends to permit movement of said first and second arms relative to one another;
   (C) a first blade positioned proximate said first arm support shaft end, including a mounting end mounted to said first arm support shaft end and a free insertion end; and
   (D) a second blade positioned proximate said second arm support shaft end, including a mounting end mounted to said second arm support shaft end and a free insertion end, said first and second blades being generally parallel, whereby said first and second blades are in generally opposed relation and whereby, as said gripping ends move relative to one another, said blades move relative to one another;
   each said blade defining superior and inferior longitudinal edges, and, as said support shaft ends move apart, said superior longitudinal edges of said blades becoming transversely spaced apart from each other to a greater degree than said inferior longitudinal edges of said blades;
   distal portions of said blades proximate said insertion ends being shaped to diverge away from one another for enhanced retraction and gripping of respective adjacent vaginal walls to stabilize the orientation of said retractor relative to a vagina of a patient;
   proximal portions of said blades proximate said mounting ends being shaped to diverge away from one another to retract the labia as said blades retract respective adjacent vaginal walls;
   facing opposed longitudinal edges of said arms proximate said support shaft ends and said proximal inferior longitudinal edges of said blades cooperatively defining, when said retractor is in use, an open work area for a surgeon about the perineum and the posterior vaginal wall of a patient.

2. The retractor of claim 1 wherein said arms pivot in a plane, and said blades extend at a generally transverse angle from the plane of said arms.

3. The retractor of claim 1 wherein said blades are substantially identical and positioned proximate said support shaft ends in opposed, mirror image relationship.

4. The retractor of claim 1 wherein said insertion ends curve divergently away from each other at an included angle of about 40°.

5. The retractor of claim 4 wherein said mounting ends curve divergently away from each other at an included angle of about 30°.

6. The retractor of claim 1 wherein said mounting ends curve divergently away from each other at an included angle of about 30°.

7. The retractor of claim 1 wherein said arms include clamp members interacting to releasably maintain said arms in a manually adjusted, fixed orientation.

8. The retractor of claim 1 wherein each said arm defines peripheral flanges longitudinally extending intermediate said gripping end and said support shaft end and a series of longitudinally spaced ribs extending transversely between said peripheral flanges to rigidify said arm.

9. The retractor of claim 8 wherein said arm peripheral flanges and ribs are rearwardly disposed.

10. The retractor of claim 8 wherein each said blade defines a pair of longitudinally extending peripheral flanges and a series of transversely spaced apart longitudinally extending ribs to rigidify said blade.

11. The retractor of claim 10 wherein said blade peripheral flanges and ribs are inwardly disposed.

12. The retractor of claim 1 wherein each said blade defines a pair of longitudinally extending peripheral flanges and a series of transversely spaced apart longitudinally extending ribs to rigidify said blade.

13. The retractor of claim 12 wherein said blade peripheral flanges and ribs are inwardly disposed.

14. The retractor of claim 1 wherein each said blade has an outwardly-facing surface textured for enhanced gripping.

15. The retractor of claim 1 wherein each arm and its respective blade is of unitary, one-piece, integral construction formed in a single molding operation.

16. The retractor of claim 1 formed of exclusively lightweight plastic.

17. The retractor of claim 1 wherein said gripping ends of said first and second arms are generally aligned.

18. The retractor of claim 1 wherein, as said gripping ends move together, said support ends move apart, and vice versa.

19. The retractor of claim 18 wherein, as said gripping ends move together, said superior longitudinal edges of said blades become transversely spaced apart from each other to a greater degree than said inferior longitudinal edges of said blades.

20. The retractor of claim 1 wherein said proximal inferior longitudinal edges of said blades are concavely curved to maximize said open work area.

21. The retractor of claim 1 wherein said proximal inferior longitudinal edges of said blades are concavely curved, with the radius of curvature being about 1.4 inches.

22. An episiotomy retractor comprising, in combination:
   (A) a first scissors arm, including a manual gripping end, a support shaft end, and a pivot connection intermediate said first arm ends;
   (B) a second scissors arm, including a manual gripping end generally aligned with said first arm gripping end, a support shaft end, and a pivot connection intermediate said second arm ends, said first and second arms being pivotally attached at said pivot connections whereby, as said gripping ends move together, said support shaft ends move apart, and vice versa;

(C) a first blade extending downwardly from said first arm support shaft end and defining a mounting end and a free insertion end; and (D) a second blade extending downwardly from said second arm support shaft end and defining a mounting end and a free insertion end, said first and second blades being generally parallel whereby said first and second blades are in generally opposed relation and whereby, as said gripping ends move together, said blades move apart, and vice versa;

each said blade defining superior and inferior longitudinal edges, and, as said gripping ends move together, said superior longitudinal edges of said blades becoming transversely spaced apart from each other to a greater degree than said inferior longitudinal edges of said blades;

said insertion ends curving divergently away from one another for enhanced retraction and gripping of respective adjacent vaginal walls to stabilize the orientation of said retractor relative to a vagina;

said mounting ends curving divergently away from one another to retract the labia as said blades retract respective adjacent vaginal walls;

said pivot connections, facing opposed longitudinal edges of said arms intermediate said pivot connections and said support shaft ends, and said inferior longitudinal edges of said blades cooperatively defining, when said retractor is in use, an open work area for a surgeon about the perineum and the posterior vaginal wall;

said arms being pivotable in a plane, and said blades extending at a generally transverse angle from the plane of said arms, being substantially identical and being affixed to said support shaft ends in opposed, mirror image relationship, and said proximal inferior longitudinal edges of said blades being concavely cured to maximize said open work area.

23. The retractor of claim 22 wherein said insertion ends curve divergently away from each other at an included angle of about 40°, and said mounting ends curve divergently away from each other at an included angle of about 30°.

24. The retractor of claim 22 wherein each said arm defines peripheral flanges longitudinally extending intermediate said gripping end and said support shaft end and a series of longitudinally spaced ribs extending transversely between said peripheral flanges to rigidify said arm, said arm peripheral flanges and ribs being rearwardly disposed, and each said blade defines a pair of longitudinally extending peripheral flanges and a series of transversely spaced apart longitudinally extending ribs to rigidify said blade, said blade peripheral flanges and ribs being inwardly disposed.

25. The retractor of claim 22 wherein said arms include clamp members interacting to releasably maintain said arms in a manually adjusted, fixed orientation, and wherein each said blade has an outwardly-facing surface textured for enhanced gripping, each arm and its respective blade being of unitary, one-piece, integral construction formed in a single molding operation.

* * * * *